United States Patent [19]

Lewis

[11] 4,167,185

[45] Sep. 11, 1979

[54] FACE MASK SEAL

[75] Inventor: Robert D. Lewis, Coloma, Mich.

[73] Assignee: A-T-O Inc., Willoughby, Ohio

[21] Appl. No.: 788,237

[22] Filed: Apr. 18, 1977

[51] Int. Cl.² ............................................. A62B 7/00
[52] U.S. Cl. .................................................. 128/146.7
[58] Field of Search ............. 128/146 R, 146.3, 146.4, 128/146.5, 146.6, 146.7

[56] References Cited

U.S. PATENT DOCUMENTS

| | | | |
|---|---|---|---|
| 2,540,567 | 2/1951 | Bennett | 128/146 |
| 2,931,356 | 4/1960 | Schwarz | 128/146 |
| 2,939,458 | 6/1960 | Lundquist | 128/146 R |
| 3,330,273 | 7/1967 | Bennett | 128/146.7 |
| 3,330,274 | 7/1967 | Bennett | 128/146.7 |
| 3,343,535 | 9/1967 | Lytle et al. | 128/141 R |
| 3,545,436 | 12/1970 | Holloway | 128/146.7 X |

*Primary Examiner*—Henry J. Recla

[57] ABSTRACT

A resiliently flexible sealing element, conformable to the face of a wearer, in the form of a re-entrant flap is hingedly joined to and supported by a mask body in a spaced relationship thereto. The sealing element extends parametrically around the open side of the mask body and in selected locations thereabout is resiliently urged away from the mask body by web means disposed between the sealing element and the mask body. The web means provides pressure on the sealing surface of the sealing element directly at the deepest point on the user's face so as to eliminate the tendency of the sealing element or flap to pull away from the user's face at such selected locations.

8 Claims, 5 Drawing Figures

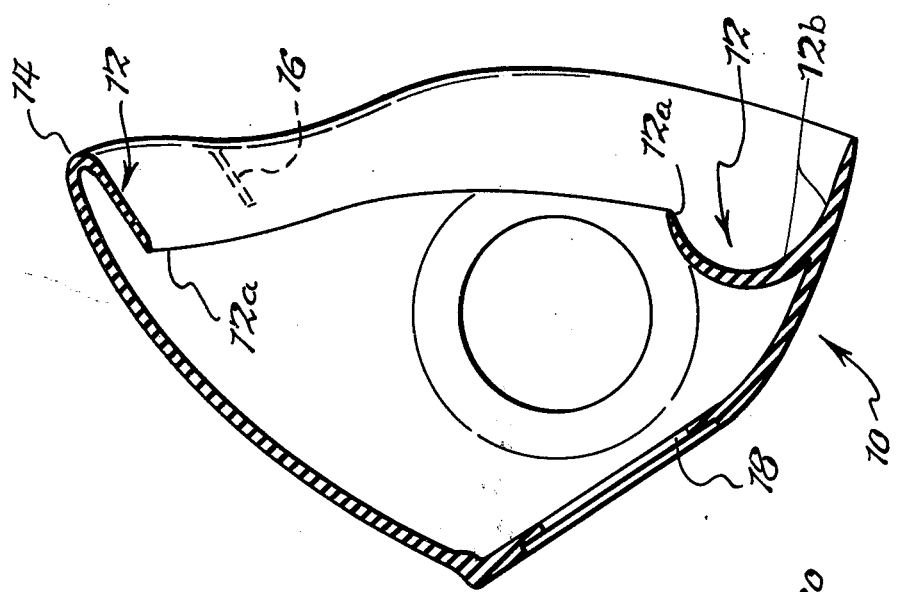
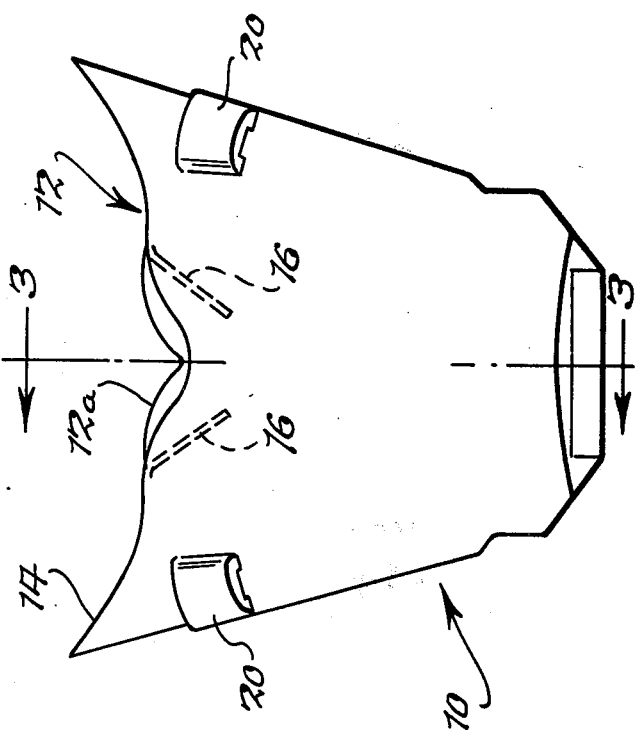
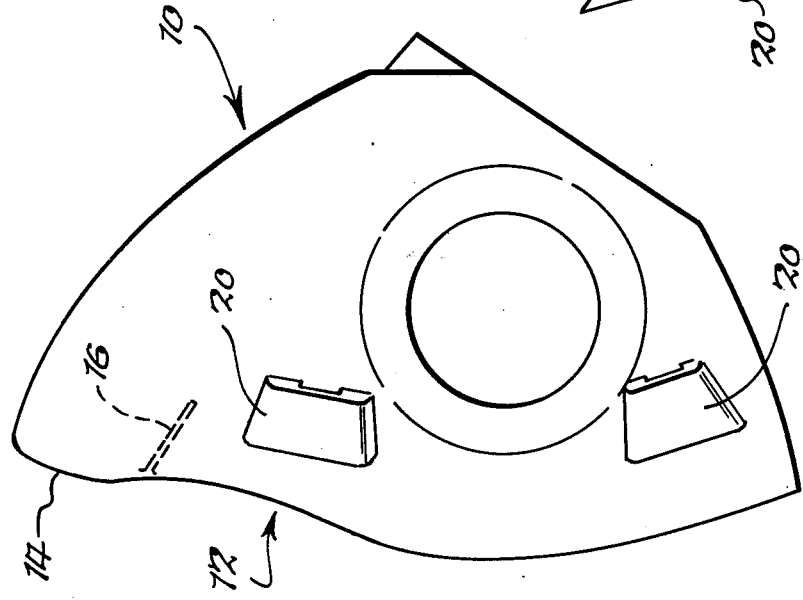

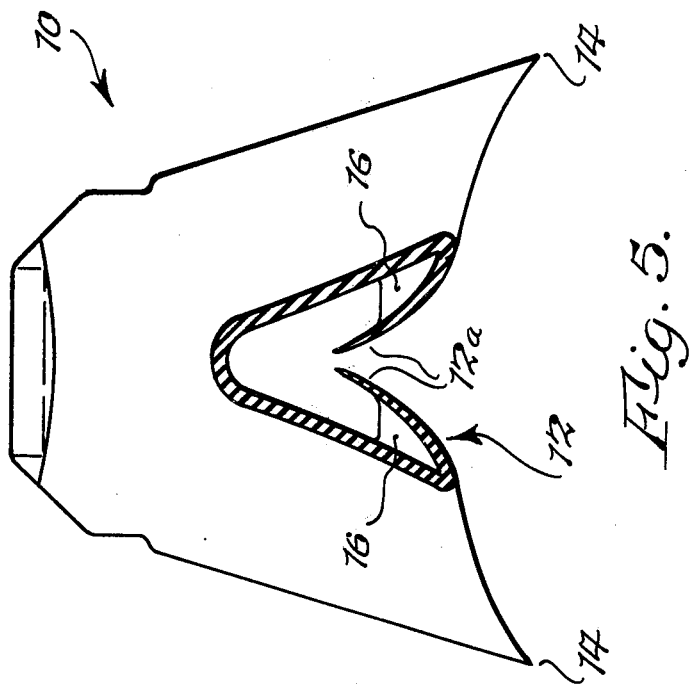
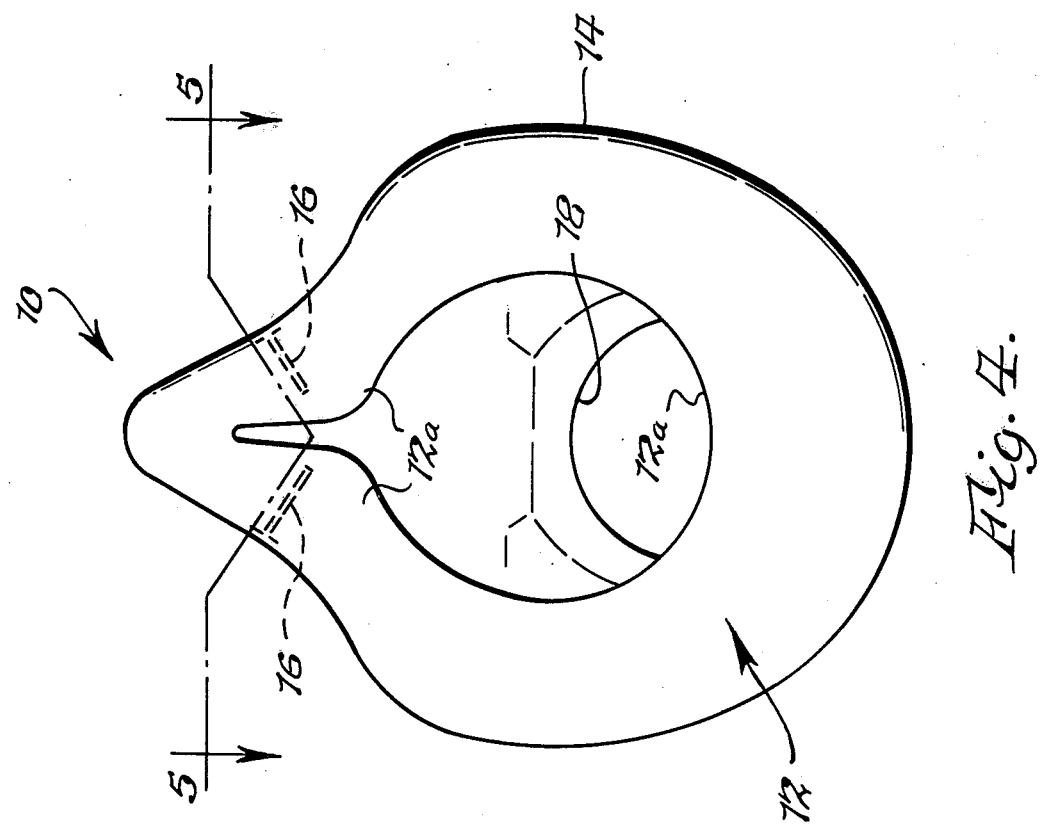

FACE MASK SEAL

BACKGROUND OF THE INVENTION

This invention relates particularly to breathing face masks which seal against the face of a user and exclude the ambient environment from those portions of the face which are confined by the mask.

It is important that a face mask properly fit the face of the wearer and the need for a good seal is self-evident. However, comfort in the fit of the mask on the face also is a significant factor because if the mask is not comfortable to wear it will bother and distract the user.

Generally, face masks are not custom made. Instead, they are made in only a very limited number of shapes and sizes, intended for use with a wide variety of facial shapes and sizes. The wide range in shapes and sizes of the human face make it difficult to provide a mask which will comfortably fit a variety of users.

U.S. Pat. No. 3,545,436—Holloway, issued Dec. 8, 1970 and pending U.S. patent application Ser. No. 707,221—Watkins filed July 21, 1976, both being assigned to the assignee of this application, disclose useful face mask arrangements in which a floating seal is suspended from a relatively rigid mask body in a manner to be comformable in sealing relation to the face of the user independently of the mask body. As the mask is positioned against the face, a hinge connecting the floating seal to the mask body resiliently yields and urges the floating seal against the face. As stated, a face piece mask or respirator should ideally fit all or most facial countours that are likely to be encountered during use. One method of accomplishing this is to provide the sealing area of the mask with a soft rolled edge or re-entrant flap. Such a soft flexible area allows the face piece to conform to the shape of the wearer's face and provide an air-tight seal. In regard to half face piece designs, a problem with respect to fitting many faces is encountered in the nose area, or more specifically, in the hollow at each side of the nose. At this point, on many faces, a sealing flap tends to be pulled away from the face at the deepest point of the hollow allowing air seepage past those two points.

SUMMARY OF THE INVENTION

A primary object of this invention is to provide a face mask seal of the foregoing type having a molded web or strut between the face mask body and the re-entrant sealing flap associated therewith so as to provide a gentle pressure on the sealing surface of the flap directly at the deepest points of the hollows on a user's face.

Another object of this invention is to provide the foregoing in a half face mask construction having a comfortable, gas-tight fit against the user's face.

Still another object of this invention is to accomplish the foregoing in a mask adapted to fit a wide variety of facial shapes and sizes, and in a construction which is practical to manufacture.

In summary, the present invention provides a face mask seal for a mask body wherein the face seal comprises a soft rolled re-entrant flap hingedly joined to the mask body adjacent to a marginal edge portion of a facial receiving cavity in the body. A thin web or strut is molded integrally to the mask body and flap at the time the entire mask body is molded so as to resiliently urge the sealing flap element against the deepest areas on the facial portion of the user.

The foregoing and other objects, advantages, and characterizing features of the present invention will become clearly apparent from the ensuing detailed description of an illustrative embodiment thereof, taken together with the accompanying drawings wherein like reference characters denote the various parts used.

BRIEF DESCRIPTION OF THE DRAWINGS

FIG. 1 is a side elevational view of a face mask, having a seal made in accordance with the instant invention;

FIG. 2 is a top plan view thereof;

FIG. 3 is a sectional view taken about on line 3—3 of FIG. 2;

FIG. 4 is a rear elevational view thereof, and

FIG. 5 is a sectional view taken about on line 5—5 of FIG. 4.

DETAILED DESCRIPTION OF A PREFERRED EMBODIMENT

Referring now in detail to the illustrative embodiment depicted in the accompanying drawings, there is shown a face mask comprising a body generally designated 10 and a seal generally designated 12, the latter being most clearly seen in FIGS. 3–5. Mask body 10 has a perimetrical edge 14 defining an opening for receiving portions of the face of a user. The sealing element 12 which is in the form of a soft rolled re-entrant flap is hingedly joined to the mask body generally adjacent to the marginal edge portion 14 about the open side of the mask body. The inner edge of the sealing element 12a accordingly is in a normally spaced relation to the mask body and overlies the same in an inwardly spaced relation with respect to the marginal edge 14. In this regard, the sealing flap 12 is generally comformable to the facial portion of a user engaged by the mask.

In addition, a web or strut 16 is molded between the mask body 10 and the sealing flap element 12 at selected locations about the perimeter of the open side of the mask body and in particular at those locations adjacent the opposite sides of a user's nose which usually corresponds to deep hollow points of varying degrees on faces of different users. The web or strut 16 may be molded at the same time as the body and sealing flap so that it does not result in any additional manufacturing or assembly cost.

The mask body is formed of a relatively rigid shape-sustaining material for enclosing, as illustrated, the lower half of a user's face, which accordingly does not interfere with a user's vision. An opening 18 is provided in the funnel portion of the mask body 10 for receiving in releasable interlocking relation therewith an air regulator device and associated air hoses, valves and filters or other related equipment, all of which can be of conventional design and are not shown.

The projections 20 are provided on the mask body 10 adjacent upper and lower opposite portions thereof, for connection with a fastening arrangement, not shown adapted to secure the face mask in place against the face of the user.

The seal 12 is of one-piece construction formed of a resiliently flexible material such as natural or synthetic rubber of a type suitable for use in the intended environment, and as stated, generally conforms to the perimetrical outline of the edge 14. The seal 12 is formed adjacent its lower end in a cup-shape to provide a chin receiving and engaging section 12b as most clearly shown in FIG. 3.

It will be appreciated that the mask body can assume other shapes, and still be used with the seal 12 and associated webs or struts 16, the particular mask body shape shown in the drawings being desirable from the view of providing unobstructed vision.

When the mask is fitted in place against the face of the user, the face engaging sealing flap 12 will resiliently yield to conform to the user's face contour as easily accommodated by the hinged connection between the flap and the mask body. The purpose of the webs or resilient struts 16 molded between the mask body wall and the sealing flap 12 is to provide a gentle pressure on the sealing surface of the flap directly at the deepest points or cavities on the user's face—this usually being on the opposite sides of the user's nasal area. The addition of the struts 16 still allows the face piece to conform to the wearer's face but provides additional pressure transmitted from the more rigid wall of the mask body to the inner sealing flap 12 exactly at the point where the sealing flap element has the tendency to pull away from the user's face. This additional pressure at the problem sealing area allows a half face piece so equipped to satisfactorily fit a greater number of varying facial shapes than a mask without such webs or struts. Necessarily, the hinged joining of the webs 16 to the mask body and sealing element allow the webs to resiliently buckle upon sufficient loading on the sealing flap.

From the foregoing, it is apparent that the objects of the present invention have been fully accomplished. As a result of this invention, an improved face mask seal is provided, particularly applicable to half face mask designs, for maintaining an effective seal about a variety of facial contours so as to prevent air seepage thereby.

Having thus described and illustrated a preferred embodiment of my invention, it will be understood that such a description and illustration is by way of example only and that such modifications and changes as may suggest themselves to those skilled in the art are intended to fall within the scope of the present invention as limited only by the appended claims.

I claim:

1. A face seal comprising, in combination with a mask body having an open side adapted to fit about a facial portion of a user, said body defining a facial portion receiving cavity defining an inner body surface and having a marginal edge portion around said open side thereof, sealing means adapted to form a seal between said body and the face of a user thereof, said sealing means comprising a resiliently flexible perimetrical sealing element in the form of a re-entrant flap joined to said body adjacent to said marginal edge portion and normally folded inwardly over said inner surface of said mask body and spaced therefrom whereby said face seal is conformable in sealing relation to a facial portion of a user independently of said body, and resilient strut-like web means extending between said sealing element and said inner surface of said body at selected locations spaced apart about the perimeter of said open side of said body and corresponding to the deepest areas of the facial portion of a user, said web means being operable to mechanically urge said sealing element against such deepest areas of the facial portion of a user.

2. A face seal according to claim 1 wherein said web means extends generally in a transverse manner relative to said sealing element and said body.

3. A face seal according to claim 1 wherein said sealing element is hingedly joined to said body generally adjacent to the marginal edge portion around said open side thereof.

4. A face seal according to claim 3 wherein said web means extends generally in a transverse manner relative to said sealing element and said body.

5. A face seal according to claim 3 wherein said web means is joined to said body and said sealing element so as to resiliently buckle upon predetermined loading on said sealing element.

6. A face seal according to claim 3 wherein said mask body is relatively rigid, shape-sustaining relative to said sealing element and said web means.

7. A face seal according to claim 3 wherein said sealing element includes a portion extending inwardly of said facial portion receiving cavity to form a socket for receiving the chin of a user.

8. A face seal according to claim 3 wherein said web means and said sealing element are of integral one-piece construction.

* * * * *